US00PP29913P3

(12) United States Plant Patent
Danziger

(10) Patent No.: US PP29,913 P3
(45) Date of Patent: Nov. 27, 2018

(54) ***PETUNIA* PLANT NAMED 'DAMORFIEST'**

(50) Latin Name: *Petunia hybrida*
Varietal Denomination: DAMORFIEST

(71) Applicant: Gavriel Danziger, Beit Dagan (IL)

(72) Inventor: Gavriel Danziger, Beit Dagan (IL)

(73) Assignee: Danziger "Dan" FlowerFarm (IL)

( * ) Notice: Subject to any disclaimer, the term of this patent is extended or adjusted under 35 U.S.C. 154(b) by 0 days.

(21) Appl. No.: 15/530,999

(22) Filed: Apr. 4, 2017

(65) Prior Publication Data

US 2018/0288927 P1 Oct. 4, 2018

(51) Int. Cl.
*A01H 5/02* (2018.01)

(52) U.S. Cl.
USPC ..... Plt./356.13

(58) Field of Classification Search
USPC ..... Plt./356.13, 356.1
CPC ..... A01H 5/02; A01H 5/00; A01H 6/1424
See application file for complete search history.

(56) References Cited

PUBLICATIONS

Fahr Greenhouses, Inc. Rooted Cuttings from Fahr Greenhouses, Inc. *Petunia* Amore Fiesta, retrieved on Mar. 29, 2018, retrieved from the Internet at http://fahrgreenhouse.com/cuttings/petunia-amore-fiesta/, one page. (Year: 2018).*

Germania Seed Early Bird Catalog 2016, retrieved on Mar. 29, 2018, retrieved from the Internet at http://germaniaseed.com/pdf/2017/2017_plant_EB_WEB.pdf, 3 introductory pages, pp. 5, 67, 194. (Year: 2016).*

* cited by examiner

*Primary Examiner* — June Hwu
(74) *Attorney, Agent, or Firm* — Cassandra Bright

(57) ABSTRACT

A new and distinct *Petunia* cultivar named 'DAMORFIEST' is disclosed, characterized by a mounded growth habit and flowers uniquely colored burgundy with yellow stripes. The plants are very well branched with a medium vigor. Light intensity and weather conditions can influence the width of the stripes, creating shapes resembling hearts. The flowers are large and plants flower abundantly. The new variety is a *Petunia*, normally produced as an outdoor garden or container plant.

2 Drawing Sheets

Figure 1:
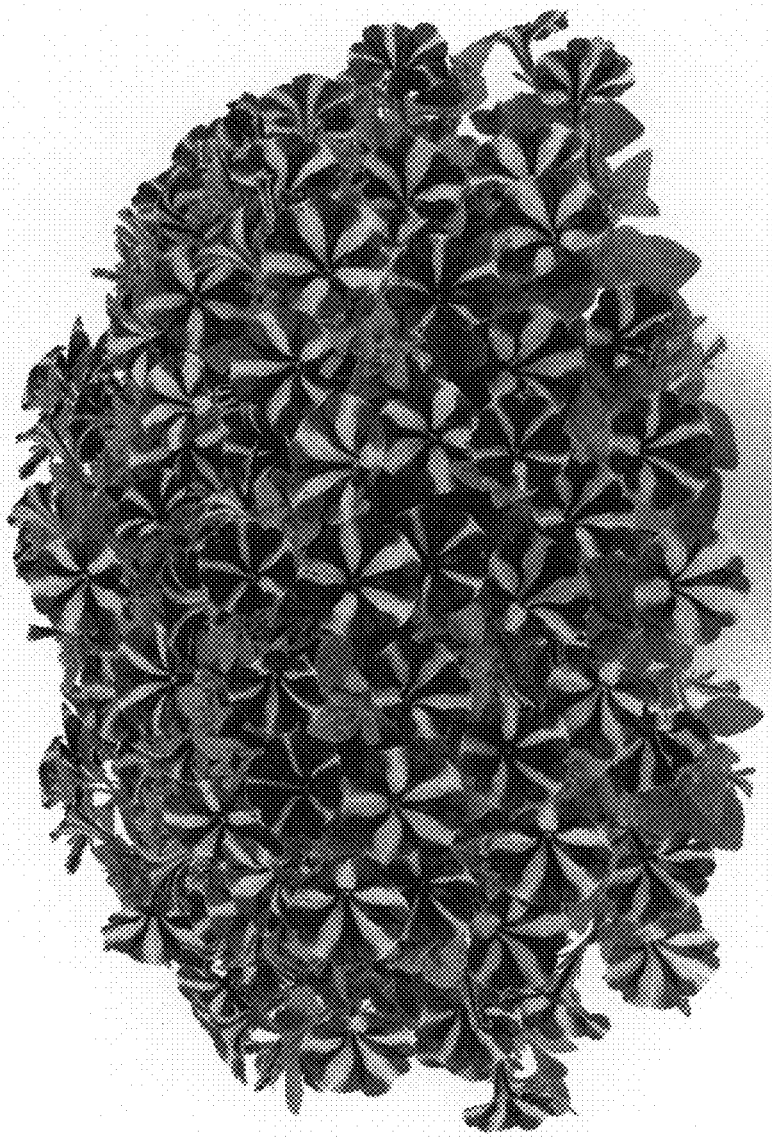

Latin name of the genus and species: *Petunia hybrida.*
Variety denomination: 'DAMORFIEST'.

BACKGROUND OF THE INVENTION

The new *Petunia hybrida* cultivar is a product of a planned breeding program conducted by the inventor, Gavriel Danziger in Moshav Mishmar Hashiva, Israel. The objective of the breeding program was to produce new *Petunia* varieties for ornamental purposes. The cross resulting in this new variety was made during December of 2013.

The seed parent is the unpatented, propriety variety referred to as *Petunia* 'cv. 12-6744'. The pollen parent is the unpatented, propriety variety referred to as *Petunia* 'cv. 12-6247'. The new variety was discovered in July of 2014 by the inventor in a group of seedlings resulting from the 2013 crossing, in a greenhouse in Moshav Mishmar Hashiva, Israel.

Asexual reproduction of the new cultivar 'DAMORFIEST' was first performed by terminal vegetative cuttings during July of 2014, at a greenhouse in Moshav Mishmar Hashiva, Israel. Subsequent propagation by has shown that the unique features of this cultivar are stable and reproduced true to type in more than 25 successive generations.

SUMMARY OF THE INVENTION

The cultivar 'DAMORFIEST' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAMORFIEST' These characteristics in combination distinguish 'DAMORFIEST' as a new and distinct *Petunia* cultivar:

1. Mounded growth habit.
2. Very well branched plant with medium vigor.
3. Flower color is burgundy with yellow stripes (light intensity and weather conditions can influence the width of the stripes, creating shapes resembling hearts).
4. Flower size is large.
5. Abundant flowering.

PARENT COMPARISON

Plants of the new cultivar 'DAMORFIEST' are similar to plants of the seed parent, *Petunia* 'cv. 12-6744' in most horticultural characteristics, however, plants of the new cultivar 'DAMORFIEST' differ in the following;

1. The new variety has a mounded growth habit, the seed parent has a semi upright growth habit.
2. The new variety is less compact, with more branches than the seed parent.
3. Flower color of the parent is yellow, the new variety is burgundy and yellow.
4. Flower size of the new variety is large, flower size of the seed parent is medium.

5. The new variety flowers more abundantly than the seed parent.

Plants of the new cultivar 'DAMORFIEST' are similar to plants of the pollen parent, *Petunia* 'cv. 12-6247' in most horticultural characteristics however, plants of the new cultivar 'DAMORFIEST' differ in the following;

1. The new variety has a mounded growth habit, the pollen parent has a semi-trailing growth habit.
2. The new variety is not as vigorous as the pollen parent.
3. Flower color of the pollen parent is burgundy with white stripes, the new variety is burgundy with yellow stripes.
4. Flower size of the new variety is large, flower size of the pollen parent is medium.
5. The new variety flowers more abundantly than the pollen parent.

COMMERCIAL COMPARISON

Plants of the new cultivar 'DAMORFIEST' can be compared to the unpatented commercial variety 'Dancas305'. These varieties are similar in most horticultural characteristics; however, 'DAMORFIEST' differs in the following:

1. Flower size of the comparator is smaller than the flower of the new variety.
2. Flower color of the comparator is purple with white stripes, while the new variety has burgundy flowers with yellow stripes.
3. Plant habit of the comparator is semi-trailing, while the new variety has a mounded growth habit.

Plants of the new cultivar 'DAMORFIEST' can also be compared to the patented commercial variety *Petunia* 'DRAY67' U.S. Plant Pat. No. 25,906. These varieties are similar in most horticultural characteristics; however, 'DAMORFIEST' differs in the following:

1. Comparator flower size is smaller than the flower of the new variety.
2. Comparator flower color is black with yellow stripes, while the new variety has burgundy flowers with yellow stripes.
3. Plants of the comparator variety are taller than plants of the new variety.

BRIEF DESCRIPTION OF THE PHOTOGRAPHS

The accompanying photograph in FIG. 1 illustrates in full color a typical plant of 'DAMORFIEST' grown in a greenhouse, in Moshav Mishmar Hashiva, Israel.

Figure 2:
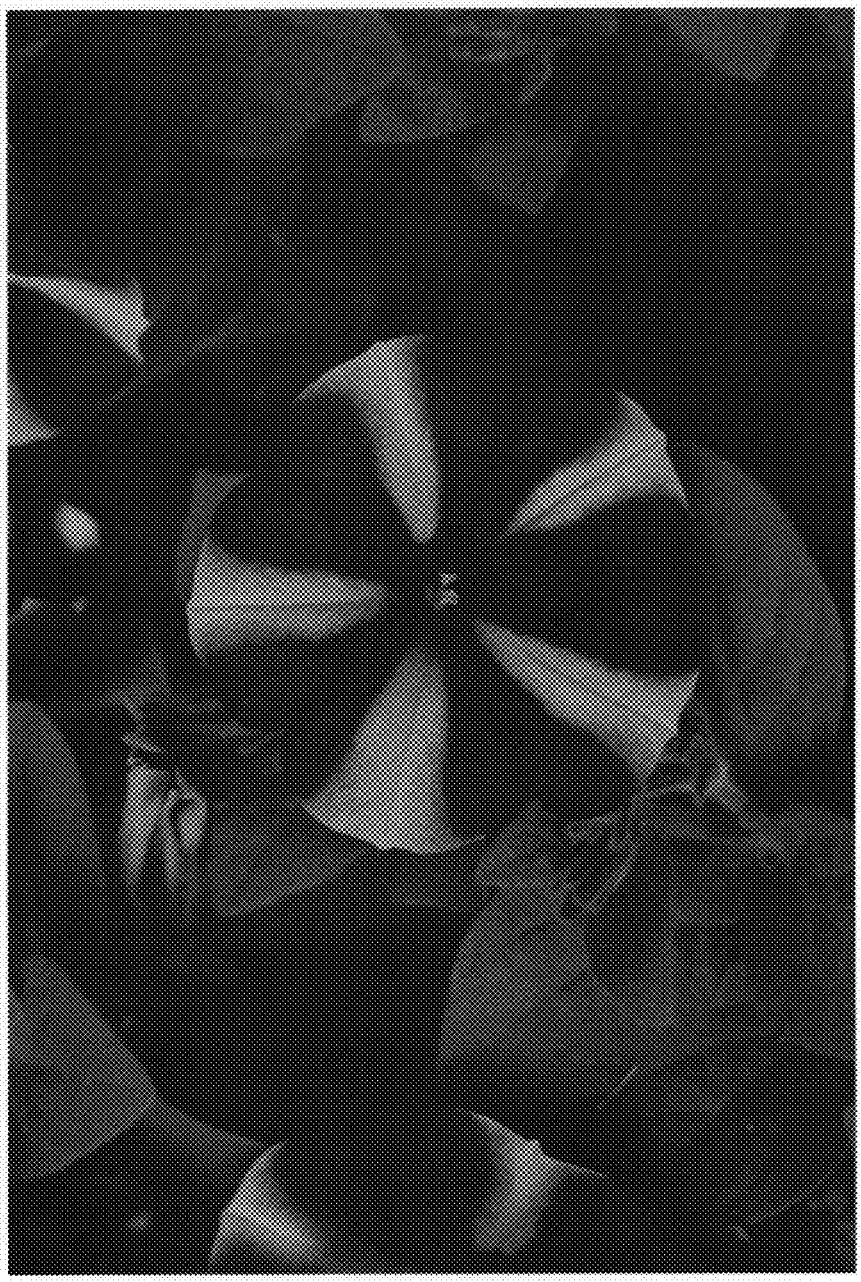

FIG. 2 illustrates in full color a typical mature flower of 'DAMORFIEST' during Spring. Age of the plant photographed is approximately 60 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DAMORFIEST' plants grown in greenhouse in Moshav Mishmar Hashiva, Israel, under natural lighting. Measurements were taken during April of 2015. The plants were approximately 90 days from a rooted cutting in a 13 cm pot. The growing temperature ranged from 20° C. to 35° C. during the days, 17° C. to 23° C. during the nights. Measurements and numerical values represent averages of typical plant types.

Botanical classification: *Petunia hybrida* 'DAMORFIEST'.

PROPAGATION

Time to initiate roots: 10-14 days at approximately 20° C.

Root description: Fibrous. Colored tan and white, not accurately measured with R.H.S. chart.

PLANT

Growth habit: Mounded.
Pot size of plant described: 13 cm.
Height: To top of flowers: About 20 cm.
Plant spread: About 55 cm.
Growth rate: Medium.
Branching characteristics: Very well branched.
Length of primary lateral branches: About 26 cm.
Diameter of lateral branches: About 0.4 cm.
Quantity of primary lateral branches: 8.
Characteristics of primary lateral branches:
*Form*.—Cylindrical.
*Diameter*.—About 0.4 cm.
*Color*.—RHS Yellow-Green 144 A.
*Texture*.—Pubescent.
*Strength*.—Good.
Internode length: About 1.5 cm.

FOLIAGE

Leaf:
*Arrangement*.—Opposite.
*Quantity*.—Approximately 28 per branch.
*Average length*.—4.0 cm.
*Average width*.—2.0 cm.
*Shape of blade*.—Elliptic.
*Apex*.—Acute.
*Base*.—Acute.
*Margin*.—Entire.
*Texture of top surface*.—Velvety.
*Texture of bottom surface*.—Velvety.
*Pubescence*.—Pubescent.
*Color*.—Young foliage upper side: RHS Yellow-Green 146 A. Young foliage under side: RHS Yellow-Green 146 B. Mature foliage upper side: RHS Yellow-Green 147 A. Mature foliage under side: RHS Yellow-Green 147 B.
*Venation*.—Type: Pinnate. Venation color upper side: RHS Yellow-Green 147 B. Venation color under side: RHS Yellow-Green 147 C.
*Petiole*.—Length: About 0.5 cm. Diameter: About 0.3 cm. Color: RHS Yellow-Green 147 B. Texture: Velvety.

FLOWER

Natural flowering season: Spring, Summer, and Autumn in Mishmar Hashiva, Israel.
Days to flowering from rooted cutting: About 30 days.
Inflorescence and flower type and habit: Axillary, single flower, salverform shape, erect habit.

Rate of flower opening: 2 to 3 days from bud to fully opened flower.

Flower longevity on plant: 3 to 6 days.

Approximate quantity of flowers per plant: About 70.

Persistent or self-cleaning: Self-cleaning.

Bud:

*Shape*.—Tubular.

*Length*.—About 4.5 cm.

*Diameter*.—About 0.8 cm.

*Color*.—RHS Yellow-green N 144 A with stripes Greyed-Purple 187 B.

Flower size:

*Diameter*.—About 5.5 cm.

*Length*.—About 2.6 cm.

*Flower tube diameter at distal end*.—About 1.1 cm.

*Flower tube diameter at proximal end*.—About 0.3 cm.

Flower:

*Lobing*.—Weak.

*Upper petal surface flower venation*.—Very weakly conspicuous.

*Inner corolla tube venation*.—Very weakly conspicuous.

*Flower corolla undulation at side view*.—Very weak.

Petals:

*Length from throat*.—About 2.2 cm.

*Width*.—About 2.8 cm.

*Quantity*.—5.

*Texture*.—Velvety.

*Apex*.—Slightly cuspidate.

*Margin*.—Entire.

Color:

*When opening*.—Upper surface: RHS Black 203 B with 5 Stripes, Yellow 9 B. Lower surface: RHS Greyed-Purple 187B with 5 Stripes, Yellow-green N144 B.

*Fully opened*.—Upper surface: Upper half of corolla lobes near Greyed-Purple 187A. Lobe base (near throat) near Black 203B, occasionally lightly streaked Greyed-Purple N187C. Sides of upper corolla (along the edge of the 187A coloration) near Purple N77A, fading out to Red-Purple N66B and 72C, both colors present individually in a moderately thick mottled stripe. Actual mid-vein colored Green 143C, surrounded by a significant stripe (about 4 to 5 mm on each side of vein) colored near Yellow 7B. Lower surface: RHS Greyed-Purple 187B with 5 Stripes Yellow 7 D. Flower throat (inside): RHS Black 203 B with 5 Stripes along midveins, Yellow 9 B. Flower throat, vein: RHS Yellow-Green 153 A. Flower tube (outside): RHS Greyed-Purple 187B with 5 Stripes along midveins, Yellow-Green 153 C. Flower tube, vein: RHS Yellow-Green 154 A.

Calyx/sepals:

*Quantity per flower*.—5.

*Shape*.—Linear.

*Length*.—About 1.8 cm.

*Width*.—About 0.3 cm.

*Apex*.—Rounded.

*Base*.—Cuneate.

*Margin*.—Entire.

*Texture*.—Velvety.

*Color*.—Upper Surface: RHS Yellow-Green 146 A. Lower Surface: RHS Yellow-Green 146 B.

Peduncle: Not present.

Pedicel:

*Length*.—About 2.0 cm.

*Diameter*.—About 0.2 cm.

*Color*.—RHS Yellow-Green 146 B.

*Orientation*.—45 degrees.

Fragrance: None.

REPRODUCTIVE ORGANS

Stamens:

*Number*.—5.

*Filament length*.—About 2 cm.

Anthers:

*Length*.—About 0.1 cm.

*Shape*.—Rounded.

*Color*.—RHS Yellow 4 D.

*Pollen*.—Color: RHS Blue-Green 115 D. Quantity: Plenty.

Pistil:

*Number*.—1.

*Length*.—About 2.0 cm.

*Style*.—Length: About 1.7 cm. Color: RHS Yellow-Green 145 C.

*Stigma*.—Shape: Rounded. Color: RHS Green 145 C. Ovary Color: RHS Yellow-Green 144 C.

OTHER CHARACTERISTICS

Seeds and fruits: About 60 Brown, rounded seeds of about 0.5 mm diameter, per one brown, conical capsule.

Disease/pest resistance: Neither resistance nor susceptibility to the normal diseases and pests of *Petunia* have been observed. Typical well known diseases include: *Botrytis cineria, Fusarium, Pythium, Phytophthora*, and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DAMORFIEST' as herein illustrated and described.

* * * * *